United States Patent
Funane et al.

(10) Patent No.: US 10,638,975 B2
(45) Date of Patent: May 5, 2020

(54) BIOLOGICAL LIGHT MEASUREMENT DEVICE

(71) Applicant: Hitachi, Ltd., Tokyo (JP)

(72) Inventors: Tsukasa Funane, Tokyo (JP); Masashi Kiguchi, Tokyo (JP); Hiroki Sato, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 405 days.

(21) Appl. No.: 15/538,680

(22) PCT Filed: Jan. 7, 2015

(86) PCT No.: PCT/JP2015/050284
§ 371 (c)(1),
(2) Date: Jun. 22, 2017

(87) PCT Pub. No.: WO2016/110969
PCT Pub. Date: Jul. 14, 2016

(65) Prior Publication Data
US 2018/0220968 A1    Aug. 9, 2018

(51) Int. Cl.
*A61B 5/00* (2006.01)
*A61B 5/026* (2006.01)
*A61B 5/1455* (2006.01)

(52) U.S. Cl.
CPC .......... *A61B 5/6844* (2013.01); *A61B 5/0261* (2013.01); *A61B 5/14553* (2013.01);
(Continued)

(58) Field of Classification Search
CPC ....... A61B 5/026; A61B 5/1455; A61B 10/00; A61B 5/0261; A61B 5/6844;
(Continued)

(56) References Cited

U.S. PATENT DOCUMENTS

| | | |
|---|---|---|
| 5,349,961 A | 9/1994 | Stoddart et al. |
| 7,072,701 B2 | 7/2006 | Chen et al. |

(Continued)

FOREIGN PATENT DOCUMENTS

| | | | |
|---|---|---|---|
| JP | 2002-143169 A | 5/2002 | |
| JP | 2002143169 | * 5/2002 | ............. A61B 10/00 |

(Continued)

OTHER PUBLICATIONS

Tsukasa Funane, et al., "Quantitative evaluation of deep and shallow tissue layers' contribution to fNIRS signal using multi-distance optodes and independent component analysis", NeuroImage 85 (2014) pp. 150-165.
(Continued)

*Primary Examiner* — Eric J Messersmith
(74) *Attorney, Agent, or Firm* — Mattingly & Malur, PC

(57) ABSTRACT

A biological light measurement device has one or more light emission means arranged on a surface of a subject, one or more light detection means arranged on the surface of the subject, a holding unit for holding the light emission means and the light detection means, a mounting jig for mounting the holding unit on the subject, and means for changing an SD distance defined by a distance between the light emission means and the light detection means. The holding unit holds the light emission means and the light detection means so that two or more types of the SD distance are configured.

14 Claims, 15 Drawing Sheets

(52) U.S. Cl.
CPC .......... *A61B 5/6803* (2013.01); *A61B 5/7203* (2013.01); *A61B 2562/0223* (2013.01); *A61B 2562/0238* (2013.01); *A61B 2562/0242* (2013.01); *A61B 2562/164* (2013.01)

(58) Field of Classification Search
CPC . A61B 5/6803; A61B 5/14553; A61B 5/7203; A61B 2562/0238; A61B 2562/0223; A61B 2562/164
See application file for complete search history.

(56) References Cited

U.S. PATENT DOCUMENTS

| | | | | |
|---|---|---|---|---|
| 2005/0107716 | A1* | 5/2005 | Eaton | A61B 5/0073 600/544 |
| 2009/0262342 | A1 | 10/2009 | Fujiwara | |
| 2013/0102907 | A1 | 4/2013 | Funane et al. | |
| 2017/0367650 | A1* | 12/2017 | Wallois | A61B 5/0075 |

FOREIGN PATENT DOCUMENTS

| | | | | |
|---|---|---|---|---|
| JP | M05-245624 | | 9/2005 | |
| JP | 2014-124381 A | | 7/2014 | |
| WO | 2007/026644 A1 | | 3/2007 | |
| WO | 2010/150751 A1 | | 12/2010 | |
| WO | WO-2010150751 A1 * | | 12/2010 | .......... A61B 5/0059 |
| WO | 2012/005303 A1 | | 1/2012 | |

OTHER PUBLICATIONS

International Search Report of PCT/JP2015/050284 dated Apr. 14, 2015.

* cited by examiner

[Fig. 1]
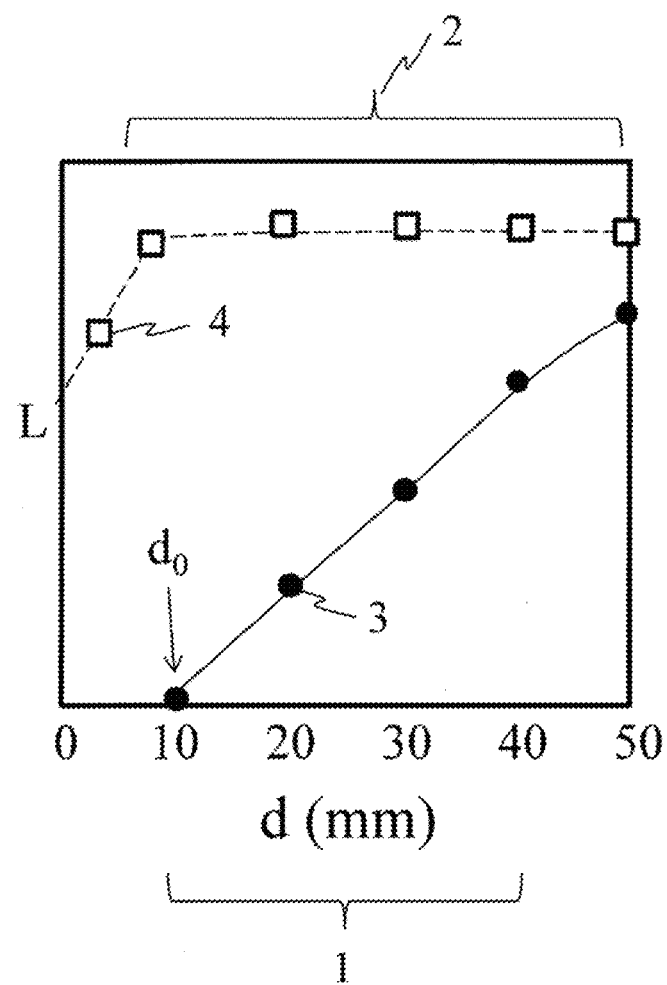
[Fig. 2]
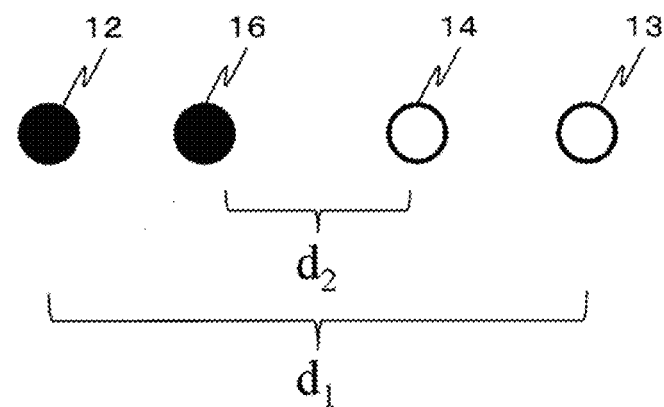

[Fig. 3]
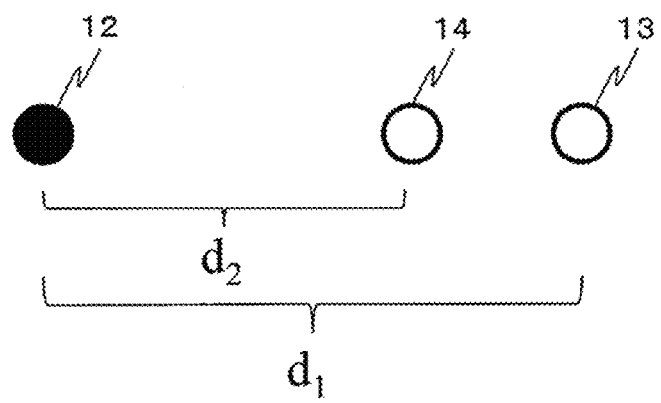
[Fig. 4]
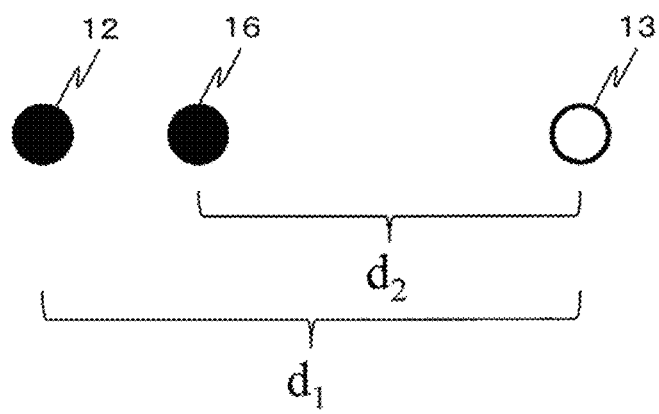

[Fig. 5]
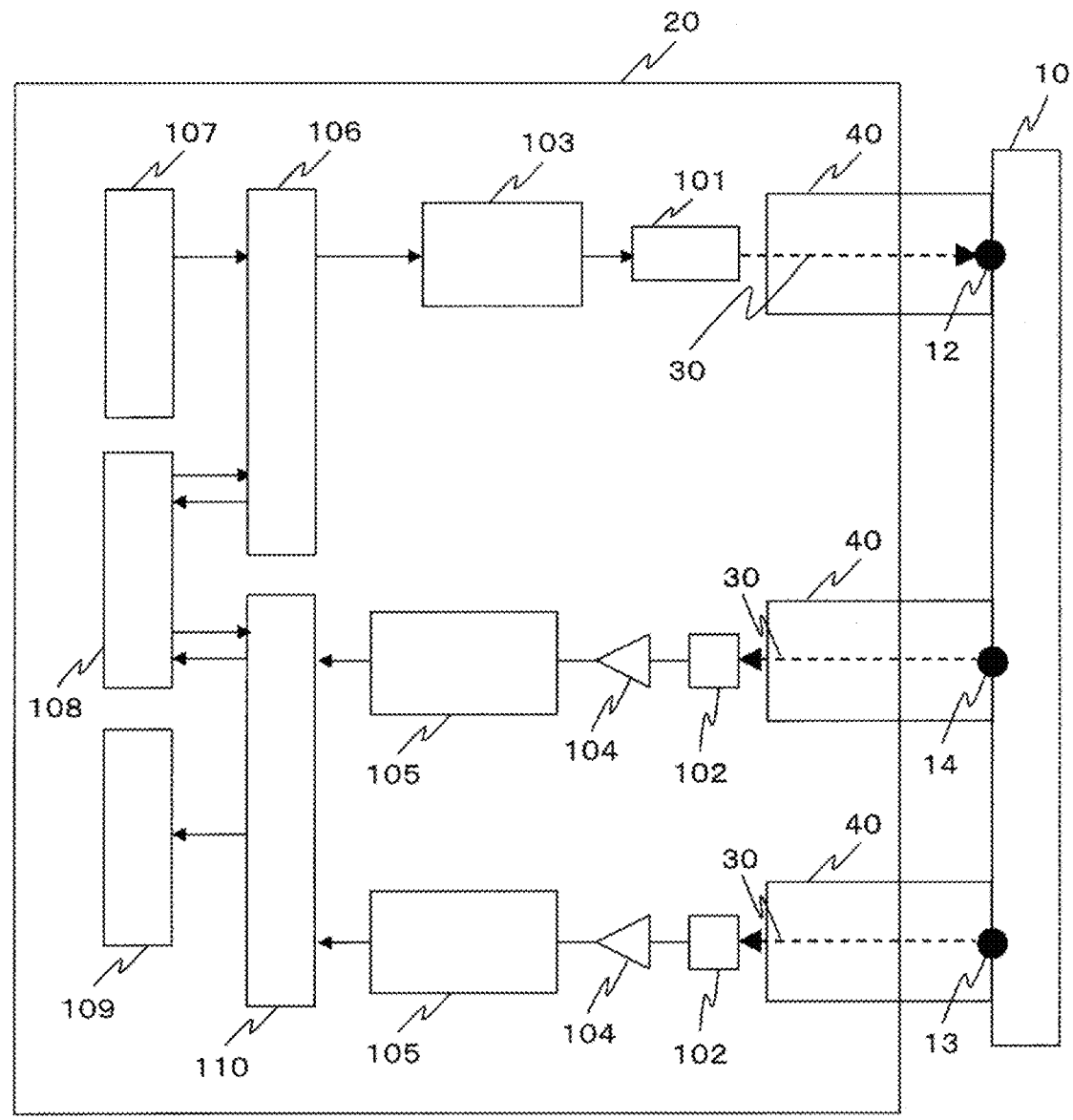

[Fig. 6]
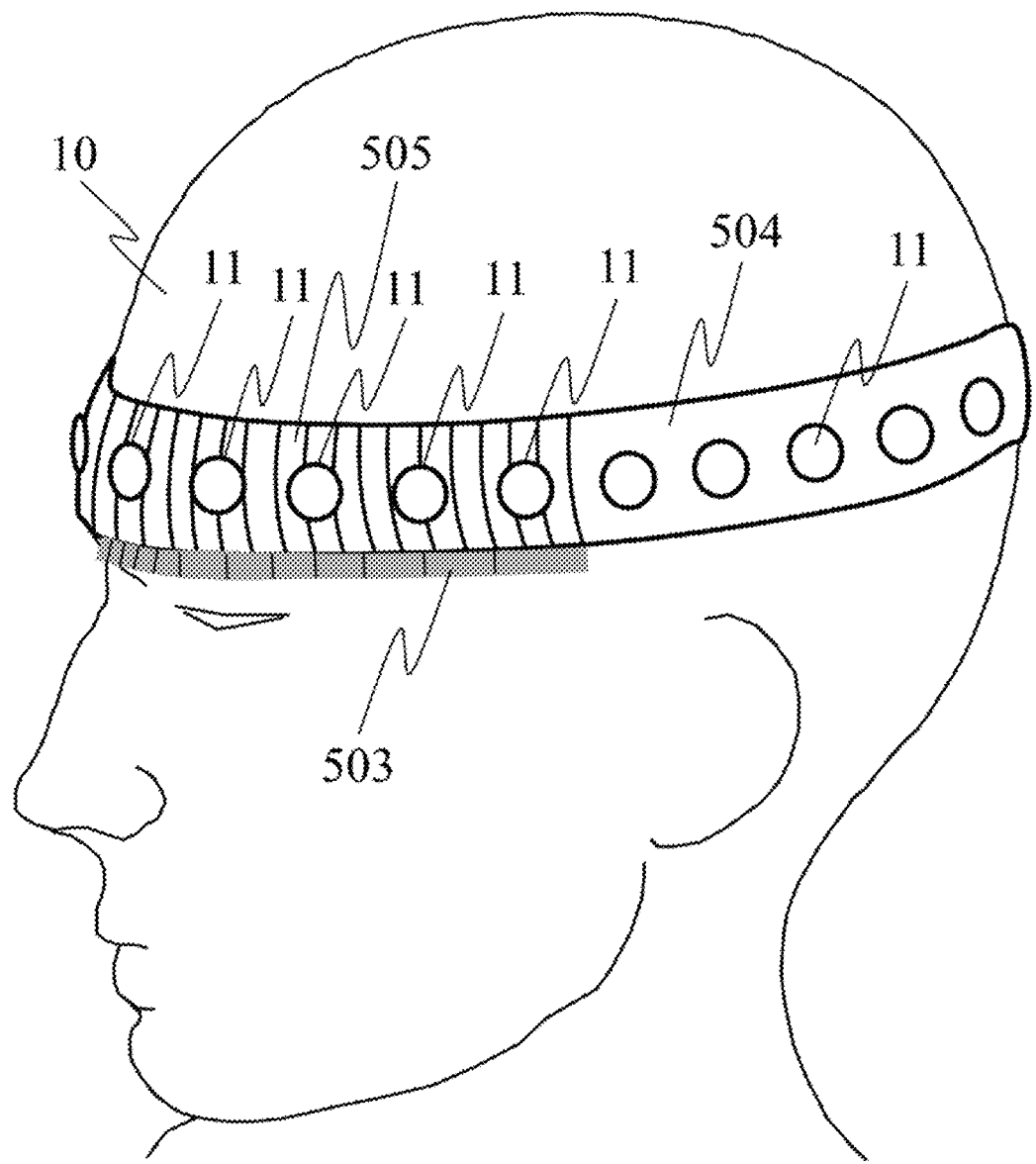

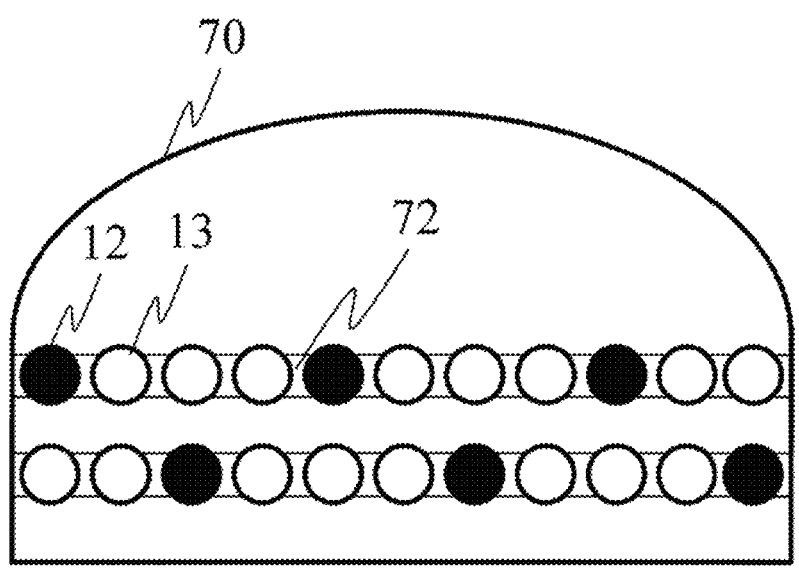
[Fig. 7]

[Fig. 8]
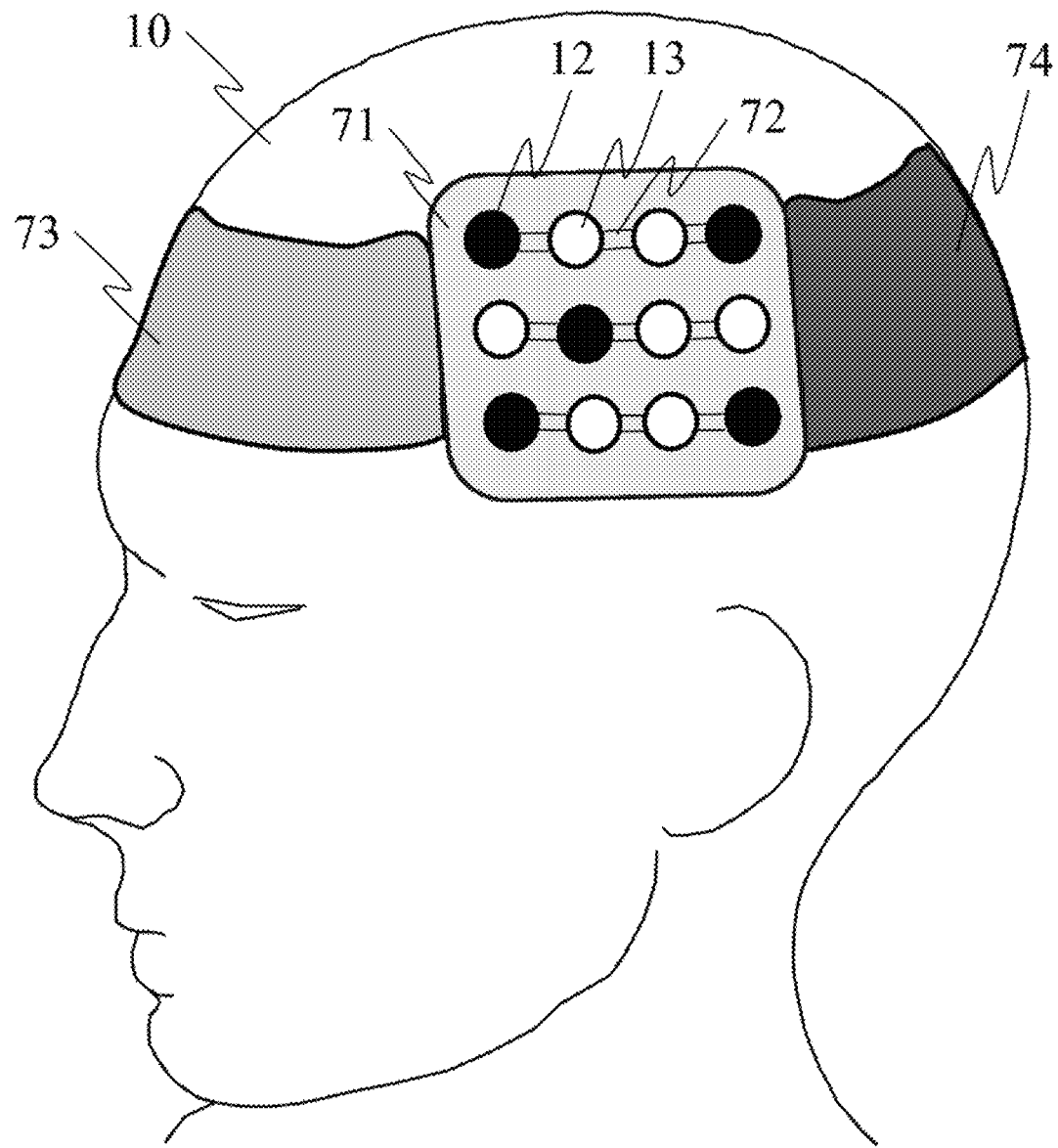

[Fig. 9]
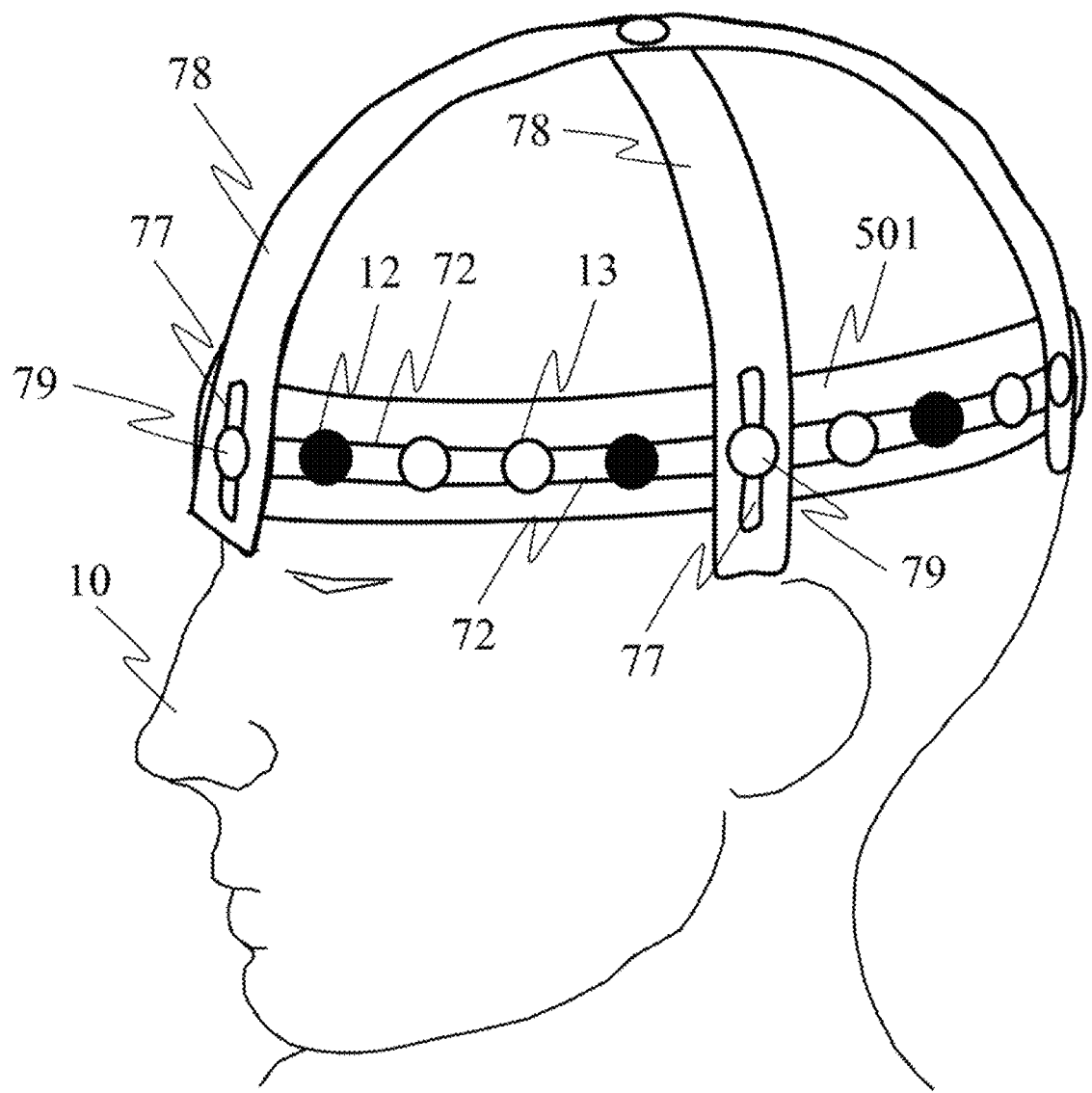

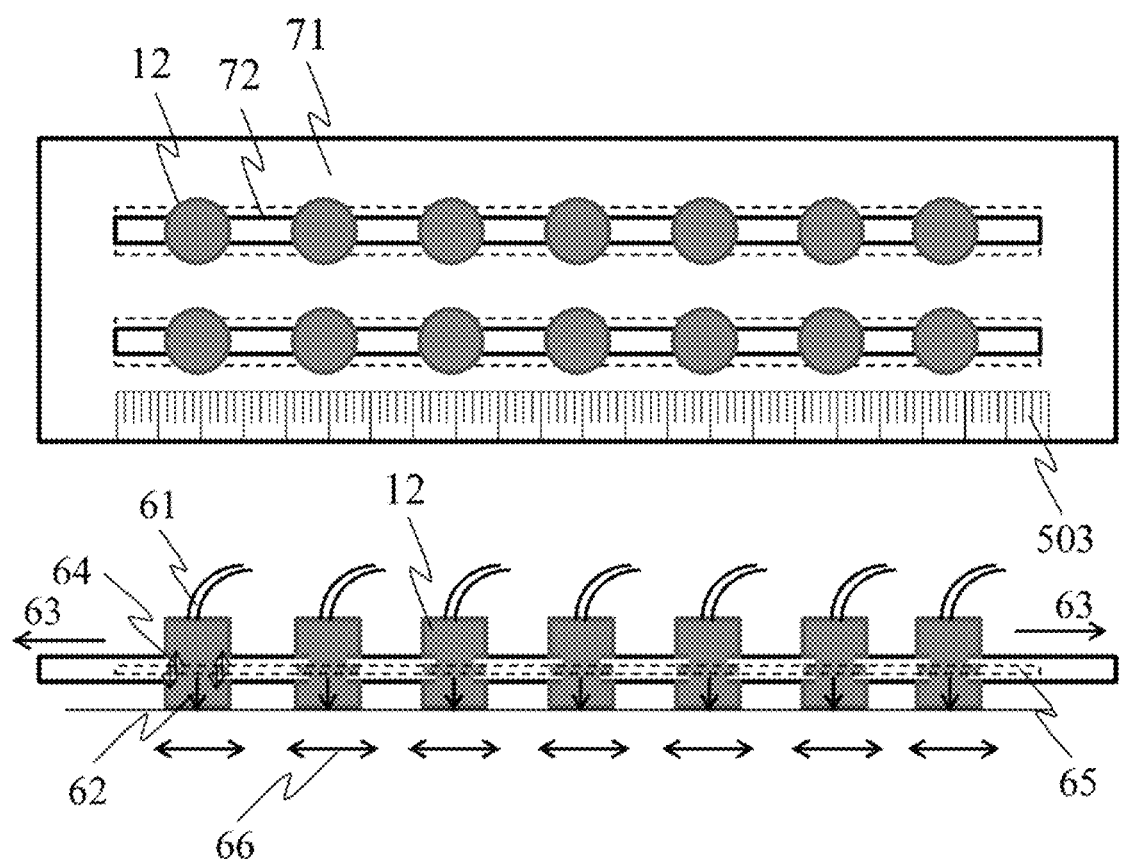
[Fig. 10]

[Fig. 11]
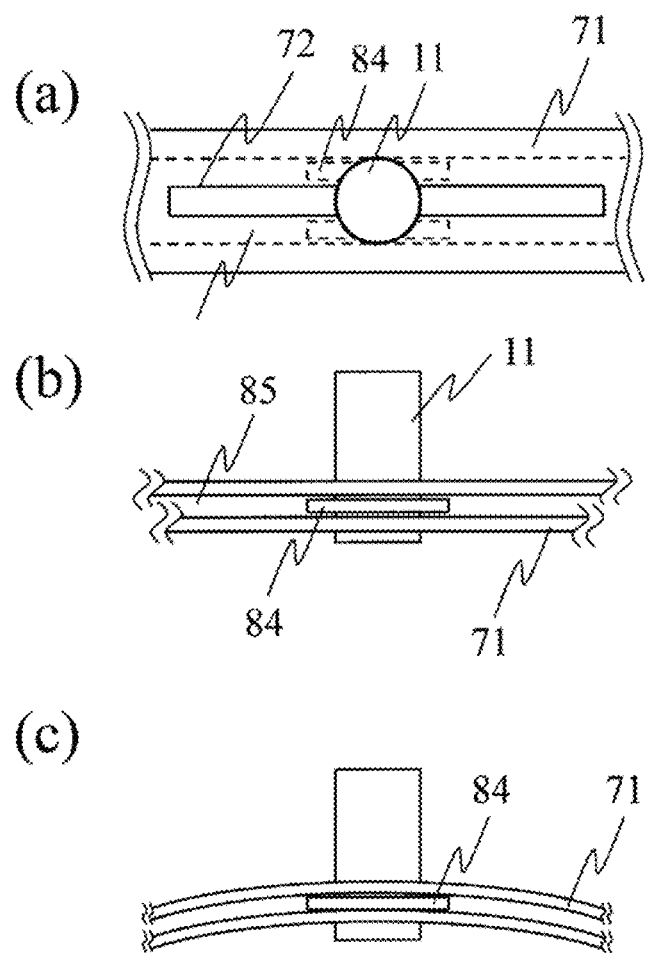

[Fig. 12]
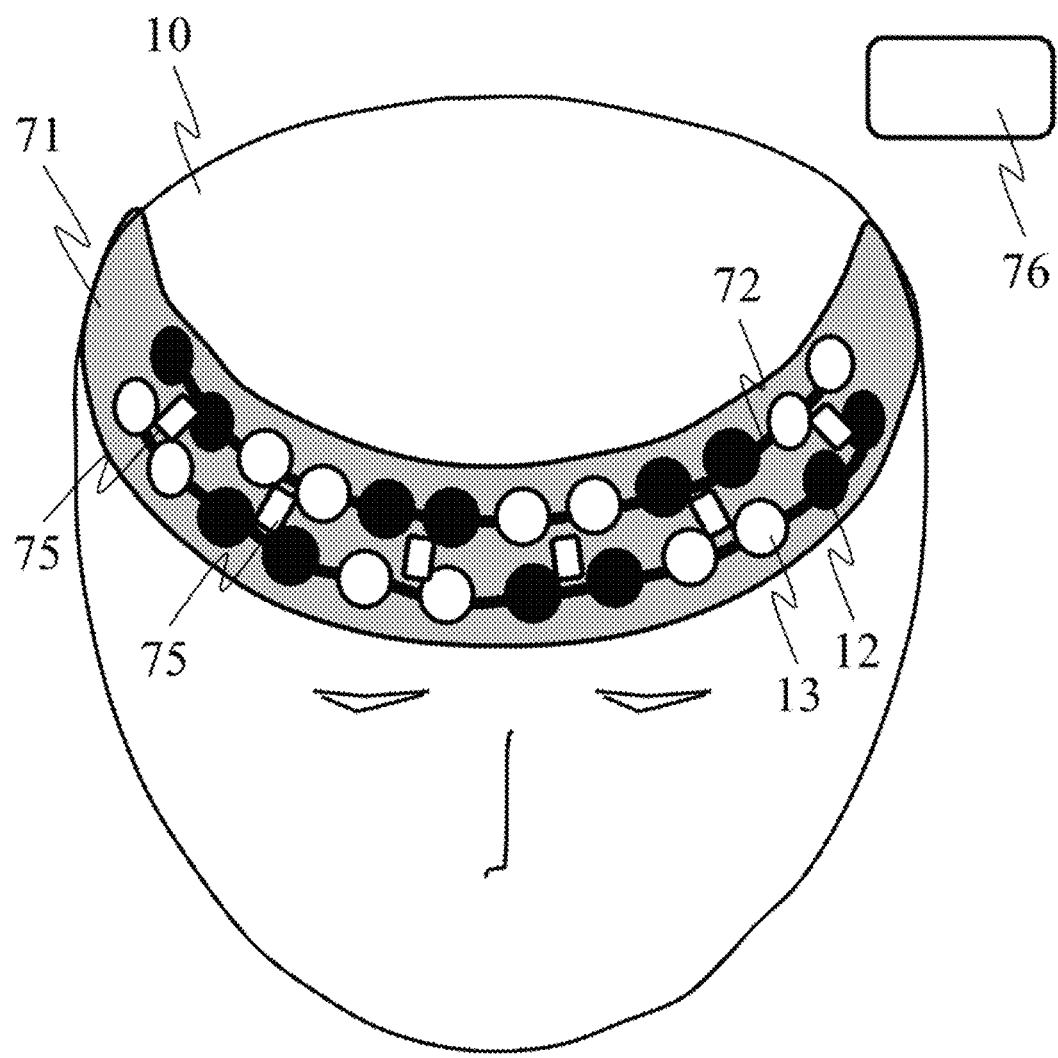

[Fig. 13]

| S\D | S1 | S2 | S3 | S4 |
|---|---|---|---|---|
| D1 | 16 | 46 | — | — |
| D2 | 29 | 31 | 30 | — |
| D3 | 43 | — | — | — |
| D4 | — | 14 | — | — |
| D5 | 30 | — | — | 31 |
| D6 | 29 | — | 31 | — |
| D7 | — | — | 14 | — |
| D8 | — | — | 16 | — |
| D9 | — | 31 | 32 | 31 |
| D10 | — | — | 43 | 14 |

[Fig. 14]
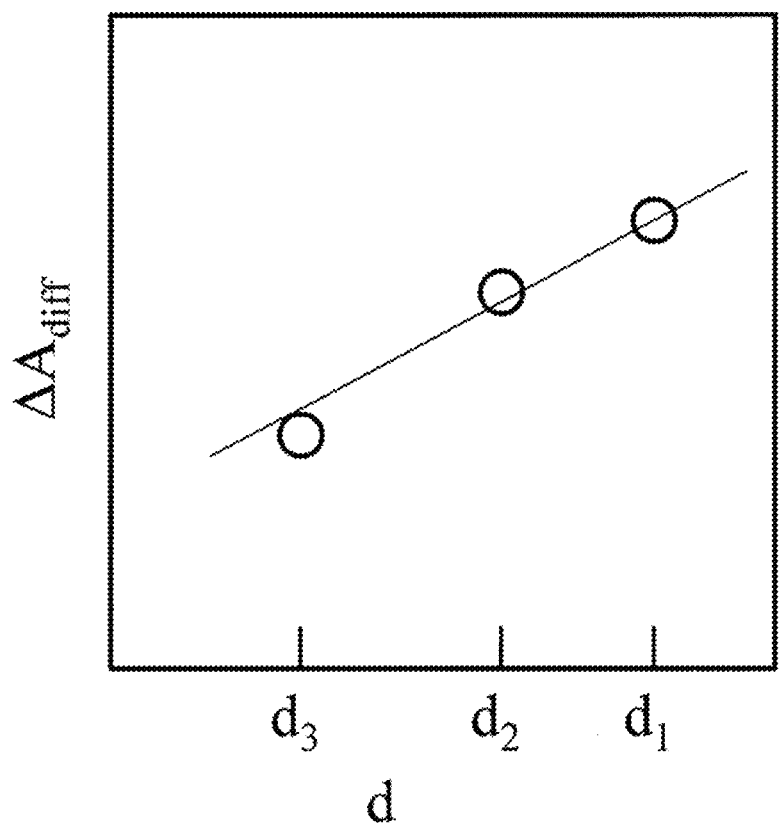

[Fig. 15]
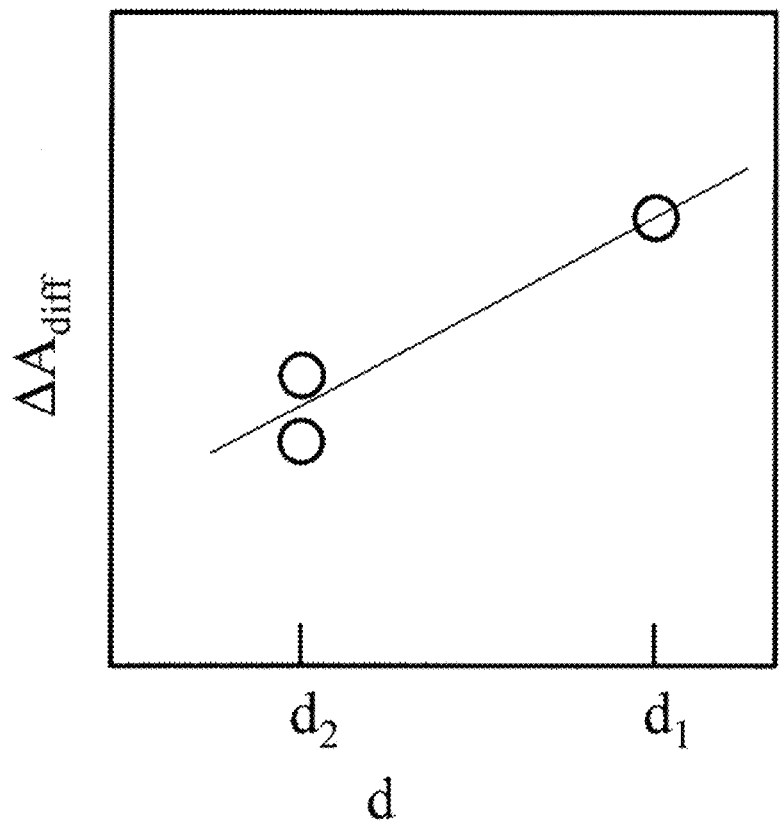

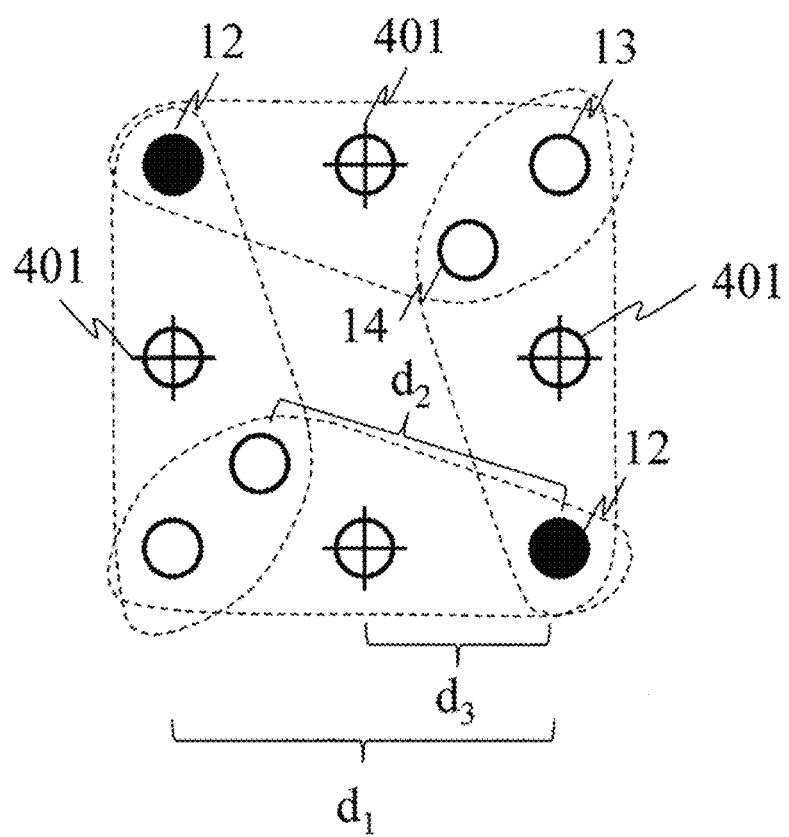
[Fig. 16]

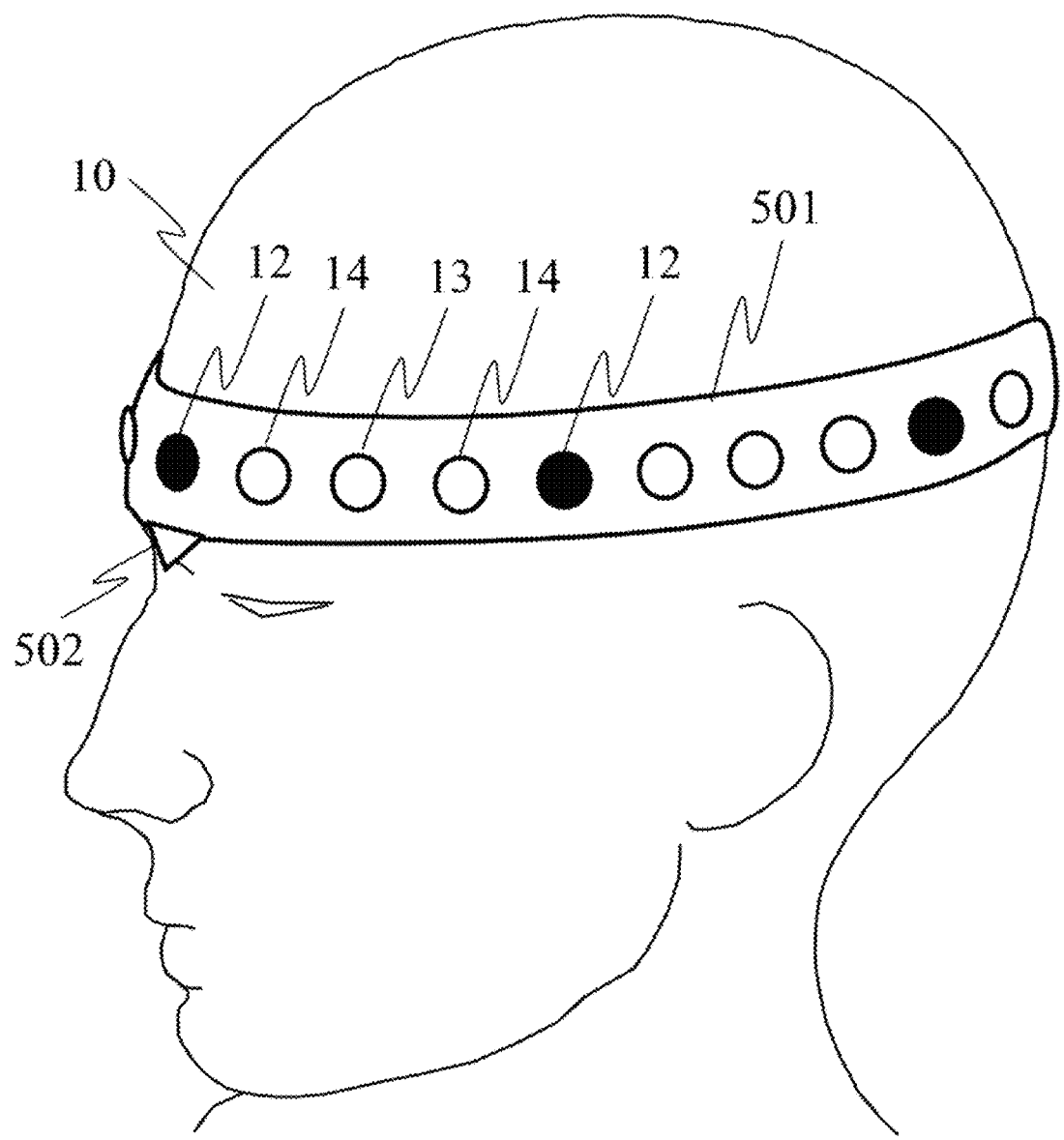
[Fig. 17]

BIOLOGICAL LIGHT MEASUREMENT DEVICE

TECHNICAL FIELD

The present invention relates to a technique for accurately measuring in-vivo information such as cerebral hemodynamic changes caused by cerebral activity, in a biological light measurement device using visible light or near-infrared light.

BACKGROUND ART

A cerebral function measurement device using a near-infrared spectroscopy (NIRS) can be used as medical and research devices, or can be used for checking an educational effect and a rehabilitation effect, health care at home, or a market survey such as product monitoring. In addition, the same method enables the cerebral function measurement device to be used for tissue oxygen saturation measurement or muscle oxygen metabolism measurement. Furthermore, the cerebral function measurement device can also be used for not only sugar content measurement of fruits but also a general absorbance spectroscopy device whose measurement target is a light scatterer.

When the cerebral function is measured using the near-infrared spectroscopy (NIRS) in the related art, in order to noninvasively observe a local hemodynamic change in the vicinity of a surface layer of a human brain, light having a wavelength belonging to a visible region to an infrared region is emitted to a subject so as to measure a light quantity passing through the inside of the subject at a position several centimeters away from a light emission position. A change amount (hereinafter, abbreviated as $\Delta CL$) in the product of hemoglobin concentration and an optical path length is measured using a modified Lambert Beer law equation. That is, according to the NIRS measurement, a change in the light quantity detected after the light is transmitted through a living body serves as a direct measurement amount, and $\Delta CL$ serves as an indirect measurement amount. In a clinical site, a language function or a visual function is measured using this method.

An optical path length L depends on a distance between a light emission position and a light detection position (hereinafter, abbreviated as an SD distance). Accordingly, $\Delta CL$ also depends on the SD distance. Therefore, there is a problem in that the measurement amount varies between devices respectively having different SD distances. On the other hand, in order to compare measurement data with each other, it is necessary to arrange the light emission position and the light detection position so that the SD distances are the same as each other. Consequently, there is a problem in that a measurement position of the brain is misaligned between subjects who respectively have different head shapes or head sizes.

Furthermore, according to a report, there is a possibility that a scalp may be affected by a skin hemodynamic change since the light is emitted to the scalp from above. Methods of extracting and removing this skin blood flow component have been studied. In many cases, measurements are performed using a plurality of SD distances. A value obtained in such a way that a measurement signal in a short SD distance is multiplied by a proper coefficient is subtracted from a measurement signal in a long SD distance, thereby removing signals derived from skin hemodynamics (for example, refer to PTLS 1 and 2). In addition, PTL 3 and NPL 1 disclose methods of obtaining a signal derived from a deep site hemodynamic change. According to this method, the signals are separated from each other by utilizing a fact that skin hemodynamic signal amplitude and deep site hemodynamic signal amplitude have mutually different SD distance dependencies. In any method, the indirect measurement amount is $\Delta CL$, and a problem has not been solved yet in that the signal amplitude depends on the SD distance.

In addition, various proposals have been made for flexible or elastic probe. However, there is no disclosed technique relating to a probe which does not depend on the SD distance and which can change and measure the SD distance, as measurement means for analyzing a measurement value reflecting the deep site hemodynamic change.

CITATION LIST

Patent Literature

PTL 1: U.S. Pat. No. 7,072,701 B2
PTL 2: U.S. Pat. No. 5,349,961
PTL 3: Pamphlet of International Publication No. WO2012/005303

Non-Patent Literature

NPL 1: T. Funane, H. Atsumori, T. Katura, A. N. Obata, H. Sato, Y. Tanikawa, E. Okada and M. Kiguchi, "Quantitative evaluation of deep and shallow tissue layers' contribution to fNIRS signal using multi-distance optodes and independent component analysis" NeuroImage 85 (1), 150 to 165 (2014)

SUMMARY OF INVENTION

Technical Problem

In a biological light measurement device capable of separating and removing skin blood flow influence inside a subject, it is important to install a probe at an optimum position of the subject. Blood vessel distribution in a surface layer differs depending on sites, and there is a significant individual difference. Therefore, it is important to set a suitable SD distance.

Solution to Problem

In order to solve the above-described problems, there is provided a biological light measurement device according to the present invention. In order to separate a signal derived from a deep site (brain) hemodynamic change and a signal derived from a skin hemodynamic change, each light emission position and each light detection position are arranged so as to realize measurement using a plurality of SD distances. In two SD distances, a logarithmic value of a detected light quantity under a certain condition or at a certain time is set to a base point, and a "change amount of the logarithmic value of the detected light quantity" at each time is measured. A gradient value with respect to "a differential SD distance of the measurement amount obtained by measuring a short SD distance from the change amount obtained by a long SD distance measurement" (hereinafter, referred to as $\Delta_{dif}/\Delta_d$) is set to a measurement amount. Then, in order to realize this configuration, the biological light measurement device has means for installing a probe at an optimum position of a subject, or means for setting a suitable SD distance, and means for measuring the SD distance.

Hereinafter, a principle assumed in the present invention will be described in detail.

FIG. 1 illustrates a result obtained by simulating a human head so as to calculate SD distance dependency of a partial optical path length 3 of a gray matter (deep site) and a partial optical path length 4 of a scalp. A horizontal axis d represents a SD distance, and a vertical axis L represents a partial optical path length. According to a graph in FIG. 1, an SD distance range 1 exists where it can be approximated that an optical path length $L_{deep}$ of the deep site linearly increases with an X-intercept $d_0$ and a gradient $L_0$. In addition, an SD distance range 2 exists where it can be approximated that an optical path length $L_{scalp}$ of the scalp is not changed.

Accordingly, if a time change of received light intensity measured in an SD distance d is set to I[d, t] in an SD distance range where the SD distance range 1 and the SD distance range 2 overlap each other, an absorbance change $\Delta A[d, t]$ at time 0 as a base point can be expressed as Expression 1 below, based on the modified Lambert Beer law equation. Here, in order to simply describe the principle of the present invention, Expression 1 exemplifies a case of measuring total hemoglobin by using the isosbestic point wavelength. A case of spectroscopically measuring oxygenated hemoglobin and deoxygenated hemoglobin by using light having two or more wavelengths will be described in the embodiment.

$$\Delta A[d, t] = \log(I[d, 0]) - \log(I[d, t]) \quad \text{[Expression 1]}$$
$$= \varepsilon \Delta C_{deep}[t] \cdot L_0(d - d_0) + \varepsilon \Delta C_{scalp}[t] \cdot L_{scalp}$$

Here, $\varepsilon$ represents a molecular extinction coefficient of total hemoglobin at the wavelength, and $\Delta C_{deep}$ and $\Delta C_{scalp}$ respectively represent a total hemoglobin concentration change in the deep site and the scalp.

A difference between $\Delta A[d_1, t]$ measured at an SD distance $d_1$ and $\Delta A[d_2, t]$ measured at an SD distance $d_2$ is obtained, and is divided by the product of a "SD distance difference" and $\varepsilon$, thereby obtaining Expression 2 below.

$$\Delta C_{deep}[t] \cdot L_0 = \frac{(\Delta A[d_1, t] - \Delta A[d_2, t])}{\varepsilon(d_1 - d_2)} \quad \text{[Expression 2]}$$

Here, the right side of Expression 2 is obtained in such a way that $\Delta A_{diff}/\Delta d$ is divided by $\varepsilon$, and the left side of Expression 2 is a new measurement amount. That is, the new measurement amount is proportional to the product of a deep site hemoglobin concentration change $\Delta C_{deep}$ and $L_0$, and skin blood flow influence ($\Delta C_{scalp} \cdot L_{scalp}$) is removed therefrom. $L_0$ is a gradient with respect to d of $L_{deep}$, and is regarded as constant. Accordingly, $L_0$ is a value which does not depend on the SD distance d. However, $L_0$ depends on an anatomical structure of the head and an optical structure depending on optical characteristic distribution.

According to the study of the present inventors, the product of $\Delta C_{deep}$ and $L_0$ can be set to an indirect measurement amount. $\Delta C_{deep}$ has a dimension of concentration, but $L_0$ is the gradient and represents a dimensionless quantity. Accordingly, this measurement amount has the dimension of concentration. In addition, in Expression 1, $\Delta C_{deep} \cdot L_0$ can be replaced with a change $\Delta (C_{deep} \cdot L_0)$ of the product of $C_{deep}$ and $L_0$. That is, even in a case where the optical structure of the head is changed, it is considered that the amount including the change is the indirect measurement amount.

In a case where $L_{deep}$ is a gray matter, referring to FIG. 1, it is understood that a SD distance range where the SD distance range 1 and the SD distance range 2 overlap each other may be approximately 10 mm to approximately 40 mm. However, even if the SD distance range is 50 mm, linearity is not greatly impaired. Accordingly, depending on allowable accuracy of measurement, the SD distance range can be 50 mm or longer. However, if the SD distance is lengthened, spatial resolution or a signal-to-noise ratio of the direct measurement amount decreases. Therefore, in actual measurement, the SD distance may be selected in accordance with a purpose. In Expression 1, the logarithmic value of the detected light quantity at one certain point time 0 is used as a reference. However, an average value of the logarithmic values of the detected light quantities at a plurality of times may be used as the reference.

Although it is assumed that the total hemoglobin change is calculated in Expression 1, an expression for calculating an oxygenated hemoglobin change or a deoxygenated hemoglobin change in the scalp and the gray matter (deep site) may be used. In addition, the new measurement amount may be defined as those which are obtained in such a way that a difference of the oxygenated or deoxygenated hemoglobin changes measured and calculated in two types of the SD distance is divided by $\varepsilon$ of the corresponding hemoglobin. In addition, here, the measurement amount is defined as an amount proportional to the deep site hemoglobin concentration change. However, the amount may not be proportional to the deep site hemoglobin concentration change by adding any offset value thereto. Even in this case, a fact is unchanged that the amount is changed in accordance with an absorber concentration change in the deep site of the subject.

According to an aspect of the present invention, a biological light measurement device has one or more light emission means arranged on a surface of a subject, one or more light detection means arranged on the surface of the subject, a holding unit for holding the light emission means and the light detection means, a mounting jig for mounting the holding unit on the subject, and means for changing an SD distance defined by a distance between the light emission means and the light detection means. The holding unit is capable of holding the light emission means and the light detection means so that two or more types of the SD distance are configured. In addition, it is preferably convenient to further include means for measuring the SD distance.

According to another aspect of the present invention, a biological light measurement device has one or more light sources that emit light to a surface of a subject, one or more detectors that detect the light reflected from the surface of the subject, and a holding unit that holds the light source and the detector, and that is configured to include a deformable material so as to be capable of changing a distance between the light source and the detector. For example, the distance between light source and the detector can be defined as a distance between an optical axis of an optical system of the light source and a center point of the detector. In addition, it is preferable to further include a mounting jig formed of a non-elastic member which is mechanically connected to the holding unit. In this case, the holding unit can be more stably mounted.

If data measured by the above-described biological light measurement device is used, it is possible to obtain a gradient value of each differential value between a change amount or a hemoglobin change amount $\Delta S1$ of a logarithmic value of light intensity measured in an SD distance d1 and a change amount or a hemoglobin change amount ΔS2 of a logarithmic value of light intensity measured in an SD distance d2, with respect to a distance between the light emission position and the light detection position. That is, by using (ΔS1−ΔS2)/(d1−d2), it is possible to obtain a value proportional to the deep site absorber concentration change in a living body or a value relating to a deep site hemodynamic change in the living body. This process can be executed by a computer which receives the data from the above-described biological light measurement device.

Advantageous Effects of Invention

According to the present invention, in the device which can obtain a measurement signal proportional to the deep site hemodynamic change without depending on the SD distance, it is possible to realize a probe holder for efficiently changing the SD distance.

An object, a configuration, and an advantageous effect except for those which are described above will be clarified by description of the following embodiments.

BRIEF DESCRIPTION OF DRAWINGS

FIG. 1 is a graph illustrating a relationship between a partial optical path length and an SD distance.

FIG. 2 is a plan view of an arrangement example of a set of a light emission position and a light detection position.

FIG. 3 is a plan view of an arrangement example of a set of the light emission position and the light detection position.

FIG. 4 is a plan view of an arrangement example of a set of the light emission position and the light detection position.

FIG. 5 is a block diagram of a device configuration example.

FIG. 6 is a perspective view illustrating a forehead and an example of a probe holder employing different members at sites other than the forehead.

FIG. 7 is a side view illustrating an example of a probe cap having a cap shape.

FIG. 8 illustrates an example of a probe holder fixing method.

FIG. 9 is a perspective view illustrating a configuration example of a support member for fixing the probe holder to a reference position.

FIG. 10 is an ambilateral view illustrating the probe holder for fixing a probe by using probe pushing pressure.

FIG. 11 is an ambilateral view illustrating a configuration for fixing the probe by bending the probe holder.

FIG. 12 is a perspective view illustrating the probe holder having a two-row arrangement for measuring an area centered on the forehead.

FIG. 13 is a plan view illustrating a screen for displaying an SD distance measurement result.

FIG. 14 is an auxiliary graph for obtaining $\Delta C_{deep}[t] \cdot L_0$.

FIG. 15 is an auxiliary graph for obtaining $\Delta C_{deep}[t] \cdot L_0$.

FIG. 16 is a plan view illustrating a relationship between the light emission position, the light detection position, and a measurement point.

FIG. 17 is a perspective view illustrating means for arranging the light emission position and the light detection position in order to perform human measurement.

DESCRIPTION OF EMBODIMENTS

Hereinafter, embodiments according to the present invention will be described with reference to the drawings. However, the present invention is not construed as being limited to description of the embodiments described below. Those skilled in the art will easily understand that a specific configuration thereof can be modified within the scope not departing from the spirit or gist of the present invention.

In configurations according to the present invention described below, the same reference numerals will be given in common to the same elements or elements having the same function in different drawings, and redundant description may be omitted in some cases.

In addition, the number for identifying configuration elements is used for each context, and the number used for one context does not necessarily indicate the same configuration in other contexts. In addition, a configuration element identified by a certain number is not precluded from functioning dually as the other configuration element identified by the other number.

In order to facilitate understanding of the invention, a position, size, shape, and range of each configuration in the drawings may not represent actual position, size, shape, and range in some cases. Therefore, the present invention is not necessarily limited to the position, size, shape, and range which are disclosed in the drawings.

Publications, patents, and patent applications cited herein plainly configure a part of the description herein.

Embodiment 1

FIGS. 2 to 4 illustrate an arrangement example of a light emission position and a light detection position according to the present embodiment. According to this configuration, it is possible to obtain a signal for calculating $\Delta A_{diff}/\Delta_d$. In each drawing, a light source is indicated by a black circle, and a light detector is indicated by a white circle.

In FIG. 2, a first light emission position 12 and a first light detection position 13 are formed in pair to leave a SD distance $d_1$ therebetween. A second light emission position 16 and a light detection position 14 of light 1 are formed in pair to leave a SD distance $d_2$ therebetween.

In FIG. 3, the light emission position 12 forms a pair with both the first light detection position 13 and the second light detection position 14. That is, the light emitted from the light emission position 12 is detected at both the first light detection position 13 and the second light detection position 14.

In FIG. 4, conversely, the light emitted respectively from the first light emission position 12 and the second light emission position 16 is detected at one light detection position 13. As illustrated in FIGS. 2 to 4, it is desirable that the light emission position and the light detection position are linearly arranged. However, in a region where a hemodynamic change can be regarded as substantially constant, it is possible to use light detection positions which are arranged in different directions and which have different SD distances. Here, a case has been described where two types of the SD distance are used as a set. However, even in a case of using three or more types of the SD distance, the light emission position and the light detection position can be similarly arranged.

FIG. 5 illustrates an example of a device configuration according to the present embodiment. In a biological light measurement device which causes light to be incident on a living body so as to detect the light scattered, absorbed, and propagated inside the living body, light 30 emitted from one or more light sources 101 included in a device body 20 is incident on a subject 10 via a waveguide 40. The light 30 is incident on the inside the subject 10 from the light emission position 12, and transmitted and propagated through the inside of the subject 10. Thereafter, the light 30 is transmitted from the light detection positions 13 and 14 located away from the light emission position 12 via the waveguide 40, and is detected at the other light detector 102. A distance between the light emission position 12 and the light detection position 13 is set to $d_1$, and a distance between the light emission position 12 and the light detection position 14 is set to $d_2$.

Here, although a case of using two light detection positions is described here, three or more light detection positions may be used. Here, one or more light sources 101 may be a semiconductor laser (LD) or a light emitting diode (LED), and one or more light detectors 102 may be an avalanche photodiode (APD), a photodiode (PD), or a photomultiplier tube (PMT). In addition, the waveguide 40 may be an optical fiber, glass, or a light guide.

The light source 101 is driven by a light source drive device 103. An output from one or more light detectors is amplified by an amplifier 104. Thereafter, the output is subjected to analog-to-digital conversion by an analog-to-digital converter 105. A result obtained by processing the converted value in an analysis unit 110 is displayed on a display unit 109, and is stored in a storage unit 108. A control unit 106 controls the light source drive device 103, based on a condition input from an input unit 107 or data of the storage unit 108.

The analysis unit 110 performs analysis, based on a signal detected by the light detector 102. Specifically, a digital signal obtained after being converted by the analog-to-digital converter 105 is received. Based on the digital signal, the following calculation is performed on deep site oxygenated hemoglobin and deep site deoxygenated hemoglobin so as to respectively obtain $(\Delta C_{oxy}L_0)_{deep}$ and $(\Delta C_{deoxy}L_0)_{deep}$. In a case where two wavelengths $\lambda 1$ and $\lambda 2$ are used as an output of the light source 101, Expression 2 can be expressed as follows.

$$\begin{pmatrix} (\Delta A^{\lambda 1}[d_1, t] - \\ \Delta A^{\lambda 1}[d_2, t]) \\ (\Delta A^{\lambda 2}[d_1, t] - \\ \Delta A^{\lambda 2}[d_2, t]) \end{pmatrix} = \begin{pmatrix} \varepsilon_{oxy}^{\lambda 1} & \varepsilon_{deoxy}^{\lambda 1} \\ \varepsilon_{oxy}^{\lambda 2} & \varepsilon_{deoxy}^{\lambda 2} \end{pmatrix} \times$$
$$\begin{pmatrix} (\Delta C_{oxy}L)_{deep}[d_1, t] + \\ (\Delta C_{oxy}L)_{scalp}[d_1, t] - \\ (\Delta C_{oxy}L)_{deep}[d_2, t] - \\ (\Delta C_{oxy}L)_{scalp}[d_2, t] \\ (\Delta C_{deoxy}L)_{deep}[d_1, t] + \\ (\Delta C_{deoxy}L)_{scalp}[d_1, t] - \\ (\Delta C_{deoxy}L)_{deep}[d_2, t] - \\ (\Delta C_{deoxy}L)_{scalp}[d_2, t] \end{pmatrix}$$
$$= \begin{pmatrix} \varepsilon_{oxy}^{\lambda 1} & \varepsilon_{deoxy}^{\lambda 1} \\ \varepsilon_{oxy}^{\lambda 2} & \varepsilon_{deoxy}^{\lambda 2} \end{pmatrix} \begin{pmatrix} (\Delta C_{oxy}[t]L_0) \\ (d_1 - d_2))_{deep} \\ (\Delta C_{deoxy}[t]L_0) \\ (d_1 - d_2))_{deep} \end{pmatrix}$$

[Expression 3]

Here, subscripts oxy and deoxy of each parameter represent that both of these are parameters corresponding to oxygenated hemoglobin and deoxygenated hemoglobin, and superscripts $\lambda 1$ and $\lambda 2$ of $\varepsilon$ represent hemoglobin molecular extinction coefficient in in each wavelength. If Expression 3 is solved for $\Delta C_{deep}L_0$, Expression 4 below is obtained.

$$\begin{pmatrix} (\Delta C_{oxy}[t]L_0)_{deep} \\ (\Delta C_{deoxy}[t]L_0)_{deep} \end{pmatrix} =$$
$$\begin{pmatrix} \varepsilon_{oxy}^{\lambda 1} & \varepsilon_{deoxy}^{\lambda 1} \\ \varepsilon_{oxy}^{\lambda 2} & \varepsilon_{deoxy}^{\lambda 2} \end{pmatrix}^{-1} \begin{pmatrix} (\Delta A^{\lambda 1}[d_1, t] - \\ \Delta A^{\lambda 1}[d_2, t])/(d_1 - d_2) \\ (\Delta A^{\lambda 2}[d_1, t] - \\ \Delta A^{\lambda 2}[d_2, t])/(d_1 - d_2) \end{pmatrix}$$

[Expression 4]

(4) A right side matrix on the right side of Expression 4 is a matrix having $\Delta A_{diff}/\Delta_d$ as an element to be used in a case where two wavelengths are measured.

Here, description is made on the assumption that the control unit 106 performs all processes such as drive of the light source 101, gain control of the light detector 102, and signal processing on a signal from the analog-to-digital converter 105. However, if the device has respectively independent control units and further has means for integrating the control units with each other, the same function can also be realized. In addition, here, although the calculation is performed after the digital conversion, the calculation may be performed in an analog manner using a logarithmic amplifier or a differential amplifier. In addition, here, although the light is propagated using the optical waveguide 40 among the light source 101, the light detector 102, and the subject 10, a configuration may be adopted in which the light source or the detector is directly brought into contact with the living body. In the present embodiment, a case of using the light source having two wavelengths has been described. However, even in a case of using one wavelength, or even in a case of using three or more wavelengths, the same calculation can be performed. In addition, in the present embodiment, one set has been described. However, similarly to the device in the related art, a plurality of sets may be measured, imaged, and displayed on the display unit 109. In addition, in the present embodiment, a case has been described where a plurality of light detectors are used for one light emitter. However, even according to a configuration where a plurality of light emitters are used for one light detector, the same advantageous effect can be obtained. In addition, a plurality of sets having different SD distances may be used without sharing the light emitter and the light detector together between the sets. However, it is possible to reduce the number of components by sharing the light emitter and the light detector together between the sets.

In a case where an output light quantity of the light emitter is changed with the lapse of time, if the output light quantity is set to $I_0[t]$ and Expression 1 is expressed using an indirect measurement amount $\Delta CL$ in the related art, the following expression is obtained.

$$\Delta A[d, t] = \log(I[d, 0]) - \log(I[d, t])$$
$$= \log(I_0[0]) - \log(I_0[t]) + \varepsilon \Delta C[t] \cdot L$$

[Expression 5]

In the case where the output light quantity of the light emitter is changed with the lapse of time, it is understood that the output light quantity is measured as a change in $\Delta CL$ since the first term and the second term on the right side in Expression 5 exist. Accordingly, according to the device in the related art, it is necessary to provide control means for stabilizing the output light quantity of the light source, that is, a circuit for detecting a portion of the output light quantity and applying negative feedback control. According to an analysis method assumed in the present invention, particularly in a case of the configuration using the plurality of light detectors for one light emitter, even if the emitted light quantity is changed as in Expression 5, terms ($I_0[0]$ and $I_0[t]$) of the emitted light quantity disappear by obtaining a difference between $\Delta A[d_1, t]$ and $\Delta A[d_2, t]$, thereby obtaining Expression 2. This means the indirect measurement amount $\Delta C_{deep} \cdot L_0$ is not affected even if the emitted light intensity is changed. Accordingly, noise or fluctuation of the light source output can be cancelled by adopting the configuration where the plurality of light detectors are used for one light emitter. Therefore, measurement accuracy is improved. Moreover, it is no longer necessary to provide the control means for stabilizing the output light quantity of the light source, which is required in the related art, thereby achieving an advantageous effect in that the device can decrease in size and the cost can be reduced. In addition, since the present method and the probe holder for realizing the present method are used, the probe can be installed in a measurement target place, even for the subjects whose head sizes are different, and it is possible to perform analysis required for removing a skin blood flow signal. In a case of the existing high density probe, the SD distances are not always unified depending on manufacturers. Even in this case, a skin blood flow signal removing method is applicable. Furthermore, until now, it is difficult to compare amplitudes with each other in a case where the SD distances are different from each other. However, there is an advantageous effect in that the amplitudes can be compared with each other between measurement points by correction using a difference between the SD distances.

As a method for realizing the measurement using the above-described probe arrangement, FIG. 6 illustrates an example of probe holders using different members for the forehead and sites other than the forehead. The forehead of the subject 10 is provided with a "probe holder formed of a plastic material or an elastic member" 505, and the sites including an occipital region other than the forehead are provided with a "probe holder formed of a non-elastic member" 504.

A probe 11 is the light source or the light detector. In order to remove skin blood flow influence in the forehead, measurement is performed using a multi-distance arrangement having the plurality of SD distances. Therefore, the SD distance is adjusted in order to employ the method according to the present embodiment.

In sites having hair (hairy sites) such as an occipital region, the skin blood flow influence is relatively small. Accordingly, here, measurement is performed using a single distance (single SD distance) without separating the skin blood flow influence. In order to easily adjust and fix the position of the probe to a reference point from a temporal region across the occipital region, the device is provided with a probe holder 504 formed of a non-elastic member. The probe holder 505 formed of a plastic material and a probe holder 504 formed of a non-elastic member are mechanically connected to each other, thereby forming an integral probe holder. Furthermore, in order to measure a mutual distance (or the SD distance) of the probes 11 to be fixed in a probe holder 505 formed of a plastic material or an elastic member or a holding unit 501, a "non-elastic member having SD distance measurement means (scale)" 503 is installed at a position in contact with the probe holder 505 formed of the plastic material or the elastic member, or at a position close for the contact.

In this manner, the visually set SD distance can be efficiently measured. The measured SD distance and a difference between the SD distances can be used for the analysis in the analysis unit 110. For example, if the probe holder 505 is formed of uniformly elastic rubber material, when the probe holder 505 is mounted on the head of the subject, the interval between the probes becomes substantially equally elastic. Accordingly, the interval is simply adjusted. Without mounting the probe on the probe holder 504, a mounting jig can be employed. In addition, the probe holder 504 and the mounting jig can be used in common.

A shallow site signal and a deep site signal in multi-distance measurement may be extracted by employing the skin blood flow influence separation method disclosed in PTL 3 and NPL 1 or a multi-distance ICA (MD-ICA) method. In a case where the deep site signal is extracted using the MD-ICA method or other methods, the amount depending on the optical path length is measured in some cases. Accordingly, in a case where the multi-distance and single distance arrangements are mixed with each other as in the present probe configuration, in order to enable data at respective measurement points to be compared with each other, it is necessary to convert the data into one type of SD distance data. In this case, the deep site signal obtained using the method such as the MD-ICA method is converted into any SD distance data. In a case of analyzing only a relative change except for absolute value information of the amplitude, it is not necessary to convert the above-described indirect measurement amount $\Delta C_{deep} \cdot L_0$ into another measurement amount.

Here, a method of converting the deep site extraction signal into any SD distance in a case where the deep site extraction signal is measured as the amount depending on the optical path length is in accordance with the following procedure, for example. When a signal change $\Delta S_A$ of the deep site absorption change measured in an SD distance $d_A$ is converted into a value $\Delta S_B$ assumed to be obtained in an SD distance $d_B$, if the SD distance dependency of the gray matter partial optical path length illustrated in FIG. 1 is considered, the conversion is expressed by Expression 6 below.

$$\Delta S_B = \frac{d_B - d_0}{d_A - d_0} \Delta S_A \qquad \text{[Expression 6]}$$

That is, since it is assumed that the value is proportional to the gray matter partial optical path length, the value is converted into the amplitude of the deep site signal (deep site absorption change signal) by using the gray matter partial optical path length. According to this conversion expression, even in a case where the measurement amount depending on the SD distance or the partial optical path length is obtained in the data of the measurement device which is measured in the different SD distance, the data can be converted into one type of SD data (for example, the SD distance of 30 mm). That is, data measured in any first SD distance can be converted into data measured in any second SD distance. This conversion process may be performed using a single computer, or may be performed using a configuration having another computer to which any element of an input device, an output device, a processing device, and a storage device is connected via a network. The data measured in the first SD distance is input from the input device, and the processing device and the storage device are used so as to cause software to perform calculation process on the data. Alternatively, a function equivalent to a function configured to include the software can also be realized by hardware such as a field programmable gate array (FPGA) and an application specific integrated circuit (ASIC).

Until now, it is difficult to fix a reference position on the brain to the same place in a plurality of subjects. However, according to the above-described configuration, even if the different SD distances are mixed with each other, it is possible to suitably acquire the deep site absorption change. Therefore, an advantageous effect is achieved in that the probe position and the measurement point can be fixed to the same place and the reference position between the plurality of subjects. In addition, for example, in a case where the measurement is simultaneously performed using the other device, an advantageous effect is achieved in that the probe for NIRS can be installed at a position which does not interfere with the other probe (for example, the probe for EEG). Furthermore, in a case where the "probe holder formed of a plastic material or an elastic member" 505 has plasticity (plastically deformability), a repulsive force is not applied thereto after deformation. Accordingly, an advantageous effect is achieved in that the probe holder 505 is easily fixed to the subject 10.

FIG. 7 illustrates an example of a probe cap 70 having a cap shape. The device is provided with a probe guide 72 for changing the SD distance by manually or automatically adjusting each of the light emission position 12, the light detection position 13, or the position of the light emitter and the light detector. For example, the probe guide 72 is a slider for holding the light emitter or the light detector so as to be slidable, and can move the light emission position 12 and the light detection position 13 along the probe guide 72. Since the probe cap 70 on which the probe guide 72 is mounted has the cap shape, an advantageous effect is achieved in that the mounting is facilitated and the device is easily fixed to the head.

FIG. 8 illustrates another example of a probe holder fixing method. The probe guide 72 is installed on the probe holder 71. The light emission position 12 and the light detection position 13 can be moved along the probe guide 72.

The probe holder 71 is fixed to the subject 10 by being connected to an elastic probe band 73 and a non-elastic probe band 74. In FIG. 8, the elastic probe band 73 and the non-elastic probe band 74 are combined with each other. If all of the bands have elasticity, there is a possibility that the probe holder may be unstably held at the reference position in the subject 10. However, since the elastic probe band 73 and the non-elastic probe band 74 are combined with each other, it is possible to easily fix the non-elastic probe band to the reference position in the subject 10. For example, according to the International 10-20 EEG electrode placement method, the lower end center of the non-elastic probe band 74 can be installed at the Oz position of the occipital region.

Depending on each subject, head shapes or head sizes are different from each other. Accordingly, even in a case where there is a difference therebetween, the elastic probe band 73 is provided with elasticity in order to install the probe holder at a fixed position from the reference position. In this manner, it is possible to offset the difference in the head shapes and sizes. In this case, a relative position from a reference point on the elastic probe band 73 is changed depending on the subject 10. However, the relative position from the reference point on the non-elastic probe band 74 is not changed. This configuration has an advantageous effect in that the probe holder 71 can be efficiently fixed to a definite place from the reference position.

As an example of another probe fixing method, FIG. 9 illustrates a support member configuration example for fixing the probe holder to the reference position.

It is conceivable to install the probe so as to be aligned with the reference point on the scalp. For example, the reference point is determined in accordance with the international 10-20 method serving as the EEG electrode placement method for the EEG measurement. In order to fix the probe to the reference point, a reference position adjusting probe support member 78 is disposed along a sagittal plane and a coronal plane for the subject 10, and is connected to and fixed to the holding unit 501 or the probe holder 71 (not illustrated) by a "probe band fixing jig also serving as the probe" 79.

A position adjustment guide 77 is disposed in the reference position adjusting probe support member 78, thereby enabling the "probe band fixing jig also serving as the probe" 79 to adjust and fix the position of the holding unit 501. In this manner, it is possible to fix the holding unit 501 or the probe holder 71 to the subject 10 so as to be aligned with the head size of the subject 10.

In this case, the light emission position 12 and the light detection position 13 can be moved along the probe guide 72. For example, both of these may be arranged at an equal interval with the "probe band fixing jig also serving as the probe" 79. Here, the SD distance is changed depending on the head shape and size of the subject 10. Furthermore, even in a case of the same subject, the SD distance may vary on the forehead side and the occipital region side. However, according to the method described herein, it is possible to suitably acquire the deep site absorption change signal of the tissues.

According to this configuration, it is possible to suitably align the probe with the reference position in the subject 10. An advantageous effect is achieved in that the probe holder can be disposed without changing the number of measurement points between the subjects. In the description herein, the holding unit 501 may be replaced with the probe holder 71.

Embodiment 2

FIG. 10 illustrates the probe holder 71 for fixing the probe by utilizing probe pushing pressure. This configuration is applicable to the configuration in FIGS. 7 and 8. Each probe (the light source or the light detector) 12 is disposed on the probe guide 72, and an optical fiber 61 is connected to each probe 12. For example, the probe guide 72 has a groove 65 formed in the probe holder 71, and a projection formed in the probe 12 is fitted into the groove 65 of the probe guide. In this manner, the probe 12 is configured to be movable on the probe guide 72 without dropping out therefrom. Before the probe holder 71 is installed in the subject 10, a frictional force (64) is small between the projection of the probe 12 and the groove 65 of the probe guide 72. Accordingly, the probe 12 can be moved on the probe guide 72 in a range of a movable area 66, and the distance between the probes and the SD distance can be adjusted. The SD distance can be measured visually by using the non-elastic member 503 having the SD distance measurement means (scale) or by using a camera.

When the probe holder 71 is installed in the subject 10, the probe holder 71 is pressed against the subject 10 by a tensile force 63, thereby generating pushing pressure 62 applied to the subject 10 from the probe 12. The pushing pressure is also applied to the probe guide 72. Accordingly, a frictional force 64 increases between the projection of the probe 12 and the groove 65 of the probe guide 72. The probe is fixed on the probe guide 72, thereby fixing the position of the probe on the probe holder 71. In order to obtain the tensile force 63, it is conceivable to form the probe holder 71 by using an elastic member such as rubber. Alternatively, it is conceivable to utilize the tensile force using the rubber by attaching the elastic member such as the rubber to the non-elastic probe holder 71. According to the above-described configuration, an advantageous effect is achieved in that an operator who performs measurement can easily adjust and fix the probe.

FIG. 11 is a view illustrating a configuration for fixing the probe by bending the probe holder 71. This configuration is applicable to the configuration in FIGS. 7 and 8. FIG. 11(a) is a plan view in a case where the probe holder 71 is not bent, and FIG. 11(b) is an elevation view in the case where the probe holder 71 is not bent. The probe 11 can move along the probe guide 72. In this case, a probe fixing member 84 connected to the probe 11 is fitted into a groove 85 in the probe holder, thereby enabling the probe 11 to stably slide along the probe guide 72. A slight gap is present between the probe fixing member 84 and the groove 85 in the probe holder. Therefore, the probe 11 can slide without being fixed.

FIG. 11(c) is an elevation view in a case where the probe holder 71 is bent. Since the probe holder 71 is bent, a contact portion is generated between the probe fixing member 84 and the groove 85 in the probe holder, thereby generating contact resistance (mechanical frictional force). Accordingly, the probe 11 is fixed. For example, the contact resistance can be adjusted by selecting a very flexible material such as plastic for the probe holder 71 and selecting a less flexible material such as metal for the probe fixing member 84. This configuration utilizes a fact that the probe holder 71 is bent or the curvature is changed when the probe holder 71 is fixed to the subject 10. At this time, the probe is automatically fixed. Accordingly, electromagnetic control is not required. In this manner, an advantageous effect is achieved in that a simple configuration enables the probe 11 to be switched between a fixed state and an unfixed state.

The fixing method of the probe is not limited to the above-described configuration. A material or a structure may be selected so that the position of the probe can be fixed by utilizing the frictional force among the probe, the probe holder, and the subject. The fixing method utilizing the frictional force is advantageously used since the operation is simple by utilizing other methods such as an adhesive.

Embodiment 3

FIG. 12 illustrates the probe holder having a two-row arrangement for measuring an area centered on the forehead. The light emission position 12 and the light detection position 13 are arranged in the probe holder 71 to be installed on the subject 10 so that the plurality of SD distances combined with each other can be measured. The light emission position 12 and the light detection position 13 are movable along the probe guide 72.

Furthermore, magnetic sensors 75 are arranged on the probe holder 71 so as to measure a magnetic field generated from magnetic field generation means 76. In this manner, it is possible to acquire a relative position relationship between the magnetic sensors in a three-dimensional space. Here, the entire probe holder 71 may be configured to include an elastic member, and a configuration may be adopted in which the SD distance can be changed. An example has been described in which the magnetic sensors 75 are arranged on the probe holder 71. However, a configuration may be adopted in which the magnetic sensors are embedded into the respective probes so as to directly measure the position of the respective probes. According to this configuration, the position of the probes can be estimated by the magnetic sensors, and it is possible to measure the SD distance by leaving an interval between the probes.

Figure 13:
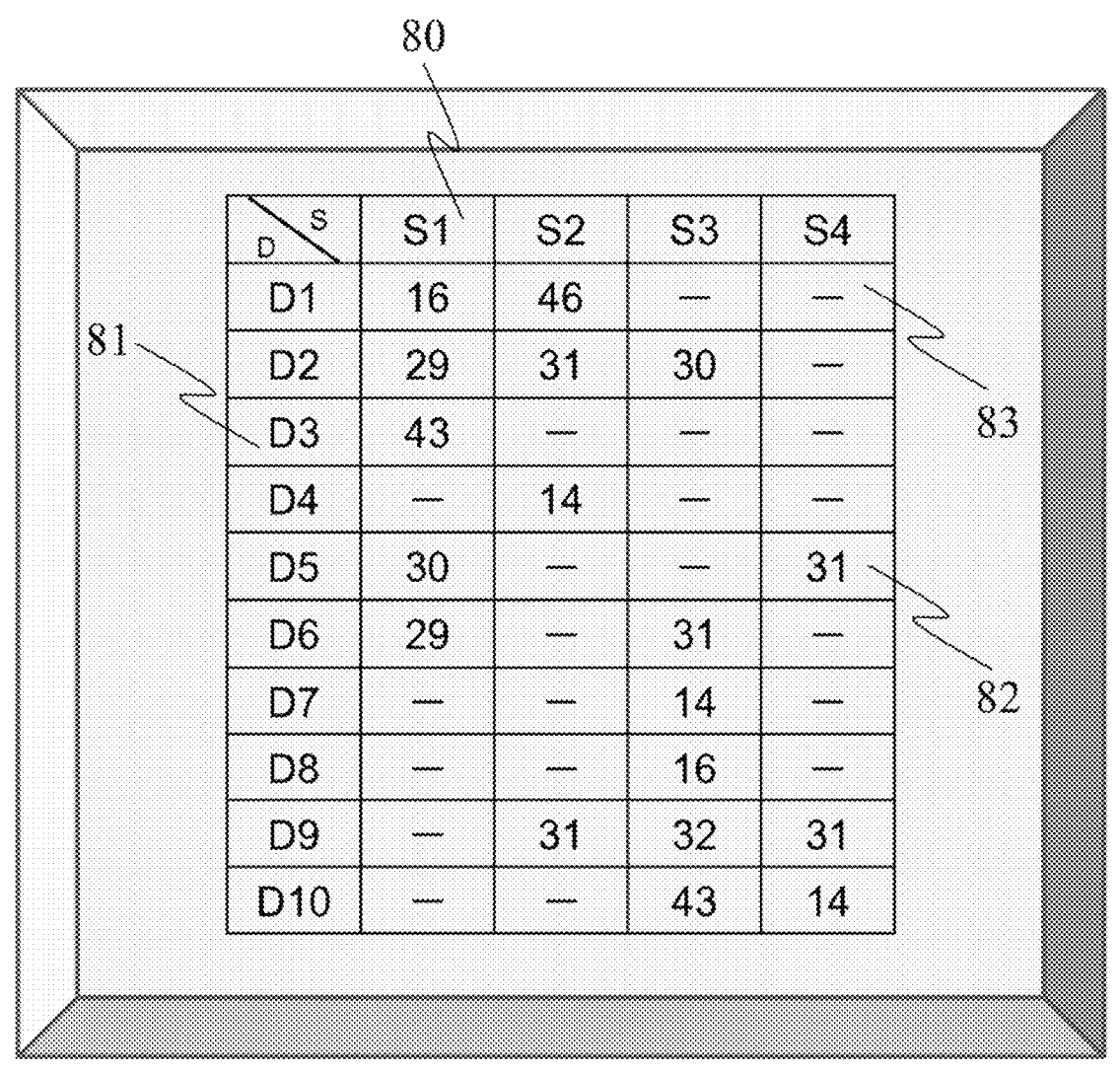

FIG. 13 illustrates an example of a screen for displaying the SD distance. This image illustrates an example in which an information processing device including an input/output device, a processing device, and a storage device is used so as to input information measured by the SD distance measurement means in the input device and to display the information on an output device. An SD distance 82 measured by the SD distance measurement means is written on a column corresponding to row indicating a corresponding light source number 80 and a line indicating a detector number 81. With regard to a pair of the light source and the detector in which the SD distance exceeds a predetermined range, or both of these are set not to be used, a symbol 83 indicating the pair of the light source and the detector not used for the measurement is written thereon.

In addition to the method using the magnetic sensor described in the present embodiment, for example, means for measuring the SD distance may be a circuit parameter located between the respective positions of light emission means and light detection means, particularly, a circuit for performing analog-to-digital conversion on a voltage to be applied to a resistance value. For example, the groove 65 of the probe guide 72 in FIG. 10 can be configured to include a conductor having predetermined resistance so as to measure the resistance value between the probe 12 and a detection electrode (not illustrated). Since the resistance value corresponds to the SD distance on a one-to-one basis, an advantageous effect is achieved in that electrical examination can be easily performed. In this case, it is necessary to provide a circuit for measuring the resistance between the respective light emission means and light detection means.

Furthermore, the means for measuring the SD distance may be configured to include a position marker disposed on the holding unit or the mounting jig, and a camera or a video device for capturing an image of the position marker. The position can be measured by using a well-known image processing technology so as to detect the position marker from the captured image. According to this configuration, it is possible to realize the measurement of the SD distance in a non-contact manner by using simple means such as the position marker. This configuration can be used in conjunction with the existing means for measuring the SD distance. In this manner, an advantageous effect is achieved in that it is possible to improve accuracy in measuring the SD distance.

Embodiment 4

Another embodiment according to the present invention will be described. Embodiment 1 mainly employs the detection signal measured in the two different SD distances $d_1$ and $d_2$. Here, calculation in a case of using three SD distances $d_1$, $d_2$, and $d_3$ as a set will be described. Three light detectors are arranged at respective positions of the SD distances $d_1$, $d_2$, and $d_3$ for one light emitter. Since two combinations of the three light detectors are three types of $d_1$-$d_2$, $d_2$-$d_3$, and $d_1$-$d_3$, three $\Delta A_{diff}[t]/\Delta d$ are obtained for each secondary set. An average value of the three values is set to $\Delta C_{deep}[t] \cdot L_0$. In this manner, a measurement error can be reduced. Here, although the three SD distances have been described, even in a case of using four or more SD distances as a set, the calculation can be similarly performed. Here, Δd of each secondary set may be the same value or may be values different from each other. In addition, in a case of a plurality of sets, Δd of each set may be the same value or may be values different from each other.

Embodiment 5

In the present embodiment, another calculation in a case of using the three SD distances $d_1$, $d_2$, and $d_3$ as a set will be described.

As illustrated in FIG. 14, at each time t, measurement values in the three SD distances are plotted on a graph in which d is set to the horizontal axis and $\Delta A_{diff}$ is set to the vertical axis. A gradient ($\Delta A_{diff}/\Delta d$) thereof is obtained using linear regression. A value obtained in such a way that the gradient is divided by ε is set to a measurement value $\Delta C_{deep}[t] \cdot L_0$. Even in this case, an advantageous effect is achieved in that the measurement error is reduced similarly to Embodiment 4.

FIG. 15 illustrates another example. FIG. 14 illustrates a case where $d_1$, $d_2$, and $d_3$ are different from each other. However, as illustrated in FIG. 15, some of $d_1$, $d_2$, and $d_3$ may have the same value. In a case of FIG. 15, an advantageous effect is achieved in that reliability of $\Delta A_{diff}$ in $d_2$ is improved and the measurement error is reduced. In addition, even in a case of using four or more SD distances as a set, the calculation can be similarly performed.

Embodiment 6

A method of imaging the measurement value of $\Delta C_{deep} \cdot L_0$ will be described with reference to FIG. 16. Light detectors 13, 14, and 15 are arranged at position away from a light emitter 12 as far as the SD distances $d_1$, $d_2$, and $d_3$, thereby forming four sets surrounded by broken lines.

FIG. 16 illustrates an example of reducing the number of the light detectors without disposing the light detector 14 on a straight line the same as that of other light detectors. The light detector 14 is shared between the sets by setting the distances from the different light emitters to be the same as each other. In a region between the light emission position and the light detection position inside the set, both the skin hemodynamic change and the cerebral hemodynamic change are respectively uniform. Accordingly, $\Delta A_{diff}$ is regarded as reflecting information between the light emission position and the light detection position farthest from the light emission position. Therefore, a substantially midpoint between the light detection position having the longest SD distance inside the set and the light emission position can be represented as a measurement point 401 of the set. When necessary, the measurement value $\Delta C_{deep} \cdot L_0$ at the measurement point (intersection of +) which is obtained for each set in this way is interpolated between the measurement points, and the image is displayed similarly to the related art. Here, although the measurement point 401 and the position of the light detector 14 overlap each other, the reason is to illustrate a case where the light detector 15 is disposed at the midpoint between the light emitter 12 and the light detector 13. The light detector 15 does not necessarily need to be disposed at the midpoint. In this case, the measurement point 401 and the position of the light detector 15 do not match each other.

As described above, within at least the two sets of the light emission position and the light detection position which are used in order to obtain the value proportional to the absorber concentration change of the subject, substantially the midpoint between the light emission position having the longest SD distance and the light detection position is set as the measurement point of the value proportional to the absorber concentration change. In this manner, the amount of hardware can be saved by using the value proportional to the absorber concentration change or means for displaying or imaging a temporal waveform thereof.

Embodiment 7

An embodiment of an arrangement of the light emitter and the light detector in the biological measurement device according to the present invention will be described with reference to FIG. 17. The light emitter 12 and the light detectors 13 and 14 are coupled by a holding unit 501 formed of an elastic mechanism or member, and in accordance with the head shape of the subject, the SD distance is elastically disposed therebetween. A marker 502 is aligned with a nose root of the subject, and another marker (not illustrated) is aligned with an external occipital protuberance. In this manner, the light emission position and the light detection position can be arranged at positions obtained by dividing the head circumference along the head shape of the subject. As an external index, an earlobe or a centromedian portion is generally used in addition to the nose root or the external occipital protuberance.

According to the embodiment described above, in the device which can obtain the measurement signal proportional to the deep site hemodynamic change without depending on the SD distance, it is possible to realize the probe holder which can efficiently change the SD distance. It is no longer necessary to arrange the optical fiber and the optical element which are normally used as the light emission means and the light detection means so that both of these keep an exact distance therebetween. In addition, both of these are more freely arranged. Accordingly, without depending on the head size or the head shape of the subject, it is possible to provide an arrangement aligned with the position of the head to be measured. Furthermore, an advantageous effect is achieved in that the measurement results can be compared with each other between the devices or measurement conditions having mutually different SD distances.

According to the device in the related art, in order to keep the SD distance constant, the light emitter and the light detector are coupled by a non-elastic member so as not to change the distance between the light emission position and the light detector position. Therefore, in the subjects having mutually different head sizes or head shapes, since the measurement position is misaligned, a brain area to be measured is misaligned. Consequently, additional work has to be carried out in order to estimate the brain area to be measured by measuring a relative position relationship among the light emission position, the light detection position, and the external index of the head of the subject. According to the present invention, it is not necessary to keep the SD distance constant. Therefore, it is possible to arrange the light emission position and the light detector position at positions relative to the head shape of the subject. The position of the brain area can be estimated at a position relative to the external index of the head of the subject. Therefore, according to the present embodiment, an advantageous effect is achieved in that it is possible to easily estimate whether the measurement position corresponds to any area of the brain. Furthermore, the measurement position is standardized, based on the external index. In this manner, an advantageous effect is achieved in that it is possible to compare and calculate measurement data obtained at the same relative position without depending on the head shape of the subject.

In addition, in the simultaneous measurement with EEG, the measurement position for EEG is disposed at the relative position based on the external index. In contrast, the optical probe for NIRS needs to be disposed at an absolute position having the fixed SD distance. Consequently, the arrangement positions of the EEG electrode and the optical probe interfere with each other, and thus, both of these are less likely to be arranged. Moreover, there is a problem in that position relationships of the measurement positions for EEG and NIRS are misaligned in each subject. The light emission position and the light detector position are arranged similarly to or in compliance with the generally used international 10-20 method for the EEG electrode arrangement. In this manner, it is possible to prevent the mutual interference. An advantageous effect is achieved in that the simultaneous measurement for EEG and NIRS is facilitated. In the present embodiment, the arrangement of the light emission position and the light detector position around the head has been described. However, it is possible to similarly configure the arrangement of the light emission position and the light detector position in a case of the entire measurement of the head or the partial measurement of the head.

In the description herein, a configuration element expressed in a singular form is intended to include a plural form, unless otherwise described in a special context.

The present invention is not limited to the above-described embodiments, and includes various modification examples. For example, a configuration of one embodiment can be partially replaced with a configuration of the other embodiment. In addition, the configuration of the other embodiment can be added to the configuration of one embodiment. In addition, with regard to a partial configuration of the respective embodiments, the other configuration can be added thereto, deleted therefrom, or replaced therewith.

INDUSTRIAL APPLICABILITY

The present invention is applicable to the biological light measurement device using visible light or near-infrared light.

REFERENCE SIGNS LIST

1: RANGE WHERE PARTIAL OPTICAL PATH LENGTH OF GRAY MATTER IS LINEAR
2: RANGE WHERE PARTIAL OPTICAL PATH LENGTH OF SCALP IS CONSTANT
3: PARTIAL OPTICAL PATH LENGTH OF GRAY MATTER
4: PARTIAL OPTICAL PATH LENGTH OF SCALP
10: SUBJECT
11: PROBE (THE LIGHT SOURCE OR LIGHT DETECTOR)
12: PROBE OR LIGHT EMISSION POSITION
13: LIGHT DETECTION POSITION
14: LIGHT DETECTION POSITION
15: LIGHT DETECTION POSITION
16: LIGHT EMISSION POSITION
20: DEVICE BODY
30: LIGHT
40: OPTICAL WAVEGUIDE
50: LIGHT EMITTER
60: LIGHT DETECTOR
61: OPTICAL FIBER
62: ARROW INDICATING PUSHING PRESSURE
63: ARROW INDICATING TENSILE FORCE
64: ARROW INDICATING FRICTIONAL FORCE BETWEEN PROBE AND PROBE HOLDER
65: PROBE GUIDE OR GROOVE IN THE PROBE HOLDER
66: ARROW INDICATING PROBE MOVABLE AREA
70: PROBE CAP
71: PROBE HOLDER
72: PROBE GUIDE
73: ELASTIC PROBE BAND
74: NON-ELASTIC PROBE BAND
75: MAGNETIC SENSOR
76: MAGNETIC FIELD GENERATION MEANS
77: POSITION ADJUSTMENT GUIDE
78: REFERENCE POSITION ADJUSTING PROBE SUPPORT MEMBER
79: PROBE BAND FIXING JIG ALSO SERVING AS THE PROBE
80: LIGHT SOURCE NUMBER
81: DETECTOR NUMBER
82: SD DISTANCE
83: SYMBOL INDICATING PAIR OF LIGHT SOURCE AND DETECTOR WHICH ARE NOT IN USE FOR MEASUREMENT
84: PROBE FIXING MEMBER
85: GROOVE IN THE PROBE HOLDER
101: LIGHT SOURCE
102: LIGHT DETECTOR
103: LIGHT SOURCE DRIVE DEVICE
104: AMPLIFIER
105: ANALOG-TO-DIGITAL CONVERTER
106: CONTROL UNIT
107: INPUT UNIT
108: STORAGE UNIT
109: DISPLAY UNIT
110: ANALYSIS UNIT
401: MEASUREMENT POINT
501: HOLDING UNIT
502: MARKER
503: NON-ELASTIC MEMBER HAVING SD DISTANCE MEASUREMENT MEANS (SCALE)
504: PROBE HOLDER FORMED OF NON-ELASTIC MEMBER
505: PROBE HOLDER FORMED OF PLASTIC MATERIAL OR ELASTIC MEMBER

The invention claimed is:

1. A biological light measurement device comprising:
one or more light emission means arranged at respective positions on a surface of a subject;
one or more light detection means arranged at respective positions on the surface of the subject;
a holding unit for holding the light emission means and the light detection means;
a mounting jig for mounting the holding unit on the subject; and
wherein the holding unit includes means for changing SD distances between the light emission means and the light detection means, and each of the SD distances is defined by a distance between the respective position of one of the light emission means and the respective position of one of the light detection means,
wherein the holding unit includes means for fixing each of the respective positions of the light emission means and the light detection means by changing frictional forces generated between the light emission means and the holding unit and between the light detection means and the holding unit which are caused by changes in pressure generated in a direction in which the holding unit is pressed against the subject, and wherein the respective positions of the light emission means and the light detection means are fixed by the means for fixing so that two or more different SD distances are configured by the light emission means and the light detection means.

2. The biological light measurement device according to claim 1, further comprising:
means for measuring the SD distances.

3. The biological light measurement device according to claim 2,
wherein the means for measuring the SD distances includes a scale disposed on the holding unit or disposed adjacent to the holding unit in order to visually measure the SD distance.

4. The biological light measurement device according to claim 2,
wherein the means for measuring the SD distances includes at least one of a magnetic sensor, an optical sensor, and an electric sensor.

5. The biological light measurement device according to claim 1,
wherein a human head is the subject,
wherein the holding unit is disposed on a forehead side of the subject, and
wherein the mounting jig is disposed on an occipital region side of the subject.

6. The biological light measurement device according to claim 1,
wherein the holding unit is formed of a flexible member, an elastic member, or a plastically deformable material.

7. The biological light measurement device according to claim 1,
wherein the mounting jig is formed of a non-elastic member.

8. The biological light measurement device according to claim 1,
wherein the means for changing the SD distances is a slider which slides at least one of the light emission means and the light detection means.

9. The biological light measurement device according to claim 1,
wherein each of the respective positions of each of the light emission means and the light detection means are fixed by a shape change of the means for fixing.

10. A biological light measurement device comprising:
a plurality of probes;
a probe holder that includes at least one probe guide in which the plurality of probes are movably held;
one or more light sources that emit light to a surface of a subject via respective ones of the probes;
one or more detectors that detect the light reflected from the surface of the subject via respective ones of the probes; and
wherein each of the probes includes a respective projection formed thereon and the at least one probe guide includes a groove in which the respective projection of each of the probes is movably held so that respective distances between the probes are changeable when the probes are in an unfixed state, and wherein the probes are switched to a fixed state at respective positions on the surface of the subject by frictional forces between the groove and the respective projection of each of the probes which are caused by a pushing pressure of the probes on the surface of the subject when the probe holder is installed on the subject.

11. The biological light measurement device according to claim 10, further comprising:
a non-elastic member having a scale disposed adjacent to the probe holder,
wherein the probe holder is formed of a flexible member, an elastic member, or a plastically deformable material,
wherein, in the unfixed state, each of the probes is movably held so that respective SD distances between the probes are changeable when the probes are in the unfixed state, each of the SD distances is defined by a distance between the respective position of one of the probes corresponding to the light sources and the respective position of one of the probes corresponding to of the detectors, and
wherein the scale is configured to measure the respective SD distances between the probes.

12. The biological light measurement device according to claim 10,
wherein the probe holder is mechanically connected to a mounting jig, and
wherein the mounting jig is formed of a non-elastic member.

13. The biological light measurement device according to claim 11,
wherein, a human head is the subject,
wherein the probe holder is disposed on a forehead of the subject, and
wherein the mounting jig is disposed on an occipital region of the subject.

14. A biological light measurement device comprising:
a plurality of probes;
a probe holder that is a plastic or elastic material and that includes at least one probe guide in which the plurality of probes are movably held;
one or more light sources that emit light to a surface of a subject via respective ones of the probes;
one or more detectors that detect the light reflected from the surface of the subject via respective ones of the probes; and
measurement means for measuring respective distances between the probes,
wherein each of the probes includes a respective projection formed thereon and the at least one probe guide includes a groove in which the respective projection of each of the probes is movably held so that the respective distances between the probes are changeable when the probes are in an unfixed state, and
wherein the probes are switched to a fixed state at respective positions on the surface of the subject by frictional forces between the groove and the respective projection of each of the probes which are caused by a pushing pressure of the probes on the surface of the subject when the probe holder is installed on the subject.

* * * * *